United States Patent [19]

Lee

[11] Patent Number: 4,895,566
[45] Date of Patent: Jan. 23, 1990

[54] COATING MEDICAL DEVICES WITH CATIONIC ANTIBIOTICS

[75] Inventor: Clarence C. Lee, Covington, Ga.

[73] Assignee: C. R. Bard, Inc., Murray Hill, N.J.

[21] Appl. No.: 208,868

[22] Filed: Jun. 15, 1988

Related U.S. Application Data

[63] Continuation of Ser. No. 889,251, Jul. 25, 1986, abandoned.

[51] Int. Cl.⁴ .............................. A61M 5/325
[52] U.S. Cl. .................................... 604/266
[58] Field of Search ................ 604/264–266, 604/268–269; 514/56, 822; 427/2; 128/335.5; 623/1, 11

[56] References Cited

U.S. PATENT DOCUMENTS

| | | | |
|---|---|---|---|
| 3,677,800 | 7/1972 | Archibald | 128/335.5 |
| 3,896,813 | 7/1975 | Kurtz | 128/335.5 |
| 3,987,797 | 10/1976 | Stephenson | 128/335.5 |
| 4,265,927 | 5/1981 | Ericksson | 514/56 |
| 4,265,928 | 5/1981 | Braun | 427/2 |
| 4,326,532 | 4/1982 | Hammar | 604/266 |
| 4,442,133 | 4/1984 | Greco et al. | 427/2 |
| 4,539,234 | 9/1985 | Sakamoto et al. | 604/265 |
| 4,678,660 | 7/1987 | McGary et al. | 604/304 |
| 4,713,402 | 12/1987 | Solomon | 604/226 |
| 4,749,585 | 6/1988 | Greco et al. | 623/1 |

OTHER PUBLICATIONS

Lubert Stryer, *Biochemistry*, 2nd Ed., published by: W. H. Freeman and Company 1981, pp. 180, 201.

*Primary Examiner*—C. Fred Rosenbaum
*Assistant Examiner*—Sharon Rose

[57] ABSTRACT

A medical device having long-lasting bactericidal properties and a method for making the same is provided. The material from which the medical device is made, the substrate, carries a negatively-charged group having a pKa of less than 6. A cationic antibiotic is ionically bonded to the negatively-charged group. The negatively-charged group may be a portion of a larger carrier molecule. The carrier molecule is bound to the substrate such that the negatively-charged group is exposed for ionic interaction with the cationic antibiotic. Heparin is an ideal carrier molecule because it has both anti-bacterial adhesion activity and anti-thrombogenic activity.

6 Claims, No Drawings

COATING MEDICAL DEVICES WITH CATIONIC ANTIBIOTICS

This application is a continuation division of application Ser. No. 06/889,251, filed July 25, 1986, now abandoned.

This invention relates to implantable medical devices having germicidal and antithrombogenic properties, and in particular relates to securing cationic antibiotics to medical devices.

BACKGROUND OF THE INVENTION

Medical procedures may fail due to complications arising from infection. Not only may an infection undermine the efficacy of the procedure, but it may be life-threatening itself.

For procedures involving implantable medical devices, avoiding infection is particularly problematic. Normally, free floating or platonic microbes in blood, tissue or organs are destroyed by antibodies, white blood cells, macrophages and antibiotics. With implants, microbes introduced pre-or intra-operatively may adhere to the foreign material of the implant and then transform into biofilm. Such biofilm consists of dormant microbes covered with a layer of glycocalyx secretion which protects the microbes from antibodies, macrophages and antibiotics. The microbes than may remain dormant as long as their proliferation into surrounding tissues can be checked by the body's immune system or systemic treatment with antibiotics. However, if the body's immune system is defective or if systemic administration of antibiotics is discontinued, the microbes may proliferate rapidly and invade surrounding tissue. For a more detailed description of biofilm, see "Bacterial Adherence and the Glycocalyx and Their Role in Musculoskeletal Infection", Cristina, A. G. and Costerton, J. W., Orthop. Clin. N. Amer., 15:517, 1984, and "Bacterial Biofilm in Persistent Penile Prosthesis Associated Infection", Nickel, J. C., Heaton, J., Morales, A. and Costerton, J. W., *The Journal of Urology*, 135:586–8, 1986.

Efforts to reduce the risk of this type of infection have included providing the implant with germicidal properties such that the microbes will be destroyed when they contact the implant. For example, implants coated with anionic antibiotics have been developed for reducing the risk of infection. To be effective, the antibiotic must be secured in a manner that preserves its germicidal activity. It is also critical that the antibiotic be secured firmly to the medical device so that its germicidal properties are localized and sufficiently long lasting.

Recent efforts have been focused on securing anionic antibiotics to medical devices. Many infectious agents, however, are resistant to the commonly available families of anionic antibiotics. The selection of cationic antibiotics is much broader than the selection of anionic antibiotics. The present invention provides a method for securing cationic antibiotics to medical devices.

Medical procedures involving implantable medical devices sometimes fail due to the thrombogenicity of the medical device. Many materials having the preferred physical characteristics for performing the functions of the medical device are thrombogenic. For example, as stated in U.S. Pat. No. 4,116,898, "polymers, both natural and synthetic, and particularly certain synthetic plastics have come to the fore as preferred materials . . . Their major drawback, however, is their thrombogenicity." To overcome this problem, antithrombogenic agents have been secured to medical devices.

For procedures involving a risk of failure both from infection and the thrombogenicity of the medical device, it has been suggested to secure both antibiotics and antithrombogenic agents side-by-side on the medical device. Doing so, however, dilutes the amount of either the antibiotic or antithrombogenic agent that can be attached to the device. This in turn reduces the germicidal and antithrombogenic properties of the medical device.

It is an object of the present invention to provide a medical device having long-lasting activity against infectious agents sensitive to cationic antibiotics.

It is a further object of the invention to provide a medical device having both enhanced germicidal activity, anti-bacterial adhesion activity and antithrombogenic activity.

It is still another object of the invention to provide a method for more firmly bonding cationic antibiotics to medical devices.

It is still another object of the invention to provide a method for binding cationic antibiotics to a wide range of materials.

It is still another object of the invention to provide a medical device with the above-mentioned properties that is inexpensive to prepare and capable of being package and stored.

According to the invention, a medical device having long-lasting bactericidal properties is provided. The material from which the medical device is made, the substrate, carries a negatively-charged group having a pKa of less than 6. A cationic antibiotic is ionically bonded to the negatively-charged group. The negatively-charged group may be a portion of a larger carrier molecule. The carrier molecule is bound to the substrate such that the negatively-charged group is exposed for ionic interaction with the cationic antibiotic. Heparin is an ideal carrier molecule because it has both anti-bacterial adhesion activity and anti-thrombogenic activity.

Also according to the invention, a method for preparing a medical device having long-lasting bactericidal properties is provided. The substrate is provided with a negatively-charged group having a pKa value of less than 6. The substrate is then soaked in a cationic antibiotic-containing solution and allowed to dry.

DETAILED DESCRIPTION OF THE PREFERRED EMBODIMENT

Medical devices according to the present invention may be fabricated from virtually any biocompatible substrate. It is only necessary that the substrate be capable of carrying negatively-charged groups having pKa values of less than 6. Dacron, latex, silicone, polyethylene and PVC have all been tested successfully.

Medical devices are provided with negatively-charged groups having a pKa of less than 6 and then are soaked in solutions of cationic antibiotics to ionically bind the cationic antibiotic to the medical device. It has been found that the negatively-charged groups having a pKa value of less than 6 will bind cationic antibiotics more firmly than negatively-charged groups having pKa values of greater than 6. This firmer bond does not impair the efficacy of the antibiotic's germicidal activity and holds the antibiotic on the medical device for an extended period of time. In particular, it has been found that sulphate groups, sulfonate groups and phosphate groups, having pKa values of less than 1, about 1 and 2.1 respectively, bind cationic antibiotic much more firmly than carboxyl groups (COOH) having a pKa value of greater than 6.

The negatively-charged groups may be manufactured into the surface of the medical device. Sulfonated polystyrene, for example, may be manufactured to carry suitably charged surface groups. Likewise, negatively charged groups may be attached directly to the surface of the medical device. Suitable techniques include the immobilization of negative groups carried on polymers or biopolymers by radiation or chemical cross-linking.

Negatively-charged groups may also be coated onto the surface of the medical device. In particular, a negatively-charged group may be a portion of a larger carrier molecule which is coated or otherwise attached onto the surface of the medical device. For example, phospholipids include both a phosphate group and at least one long hydrophobic side chain. A medical device manufactured from a hydrophobic substrate may be soaked in a solution containing the phospholipid. The hydrophobic side chain of the phospholipid will bind to the hydrophobic material in a manner to expose the phosphate group for binding with the cationc antibiotic. Any molecule generally described by the forumlas $ROSO_3^-$, $RSO_3^-$ and $ROPO_3^-$, where R is a long hydrophobic side chain is a suitable carrier molecule. For example, R may be composed substantially of carbon and hydrogen and be at least four carbon atoms long.

The most preferred carrier molecule is heparin, which is capable of binding more than one cationic antibiotic since it has many sulphate groups. In addition, the heparin has anti-bacterial adhesion and antithrombogenic activity. By coating the medical device with heparin, many more sulphate groups cover the medical device's surface providing more cationic binding sites over a given area than has heretofore been achieved. The substrate may then be packed rich with cationic antibiotic.

Once implanted, the cationic antibiotic will slowly be released from the heparin carrier molecule by dissociation. As cationic antibiotic is released, the heparin molecule is exposed. The exposed heparin is known to have antithrombogenic activity. The heparin also may prevent bacteria from adhering to the substrate thereby preventing for formation of a protective biofilm. Without a protective biofilm, the microbes are vulnerable to antibodies, white blood cells, macrophages and antibiotics. A heparin-coated substrate may reduce bacterial adherence by as much as ten fold. Heparin and its antibacterial properties are more particularly described in "Reduction of Bacterial Adherence to Latex Catheter Surface with Heparin", Ruggieri, M. R., *The Journal of Urology*, AUA Eighty-First Annual Meeting Abstract K/2, 533, 1986. Thus, a heparin carrier molecule serves three separate functions. It provides a dense packing of sulphate cationic binding sites, provides antibacterial adherence activites, and provides antithrombogenic activity.

Preferably the heparin is attached to the substrate by an anchor molecule interposed between the medical device and heparin. As described in U.S. Pat. No. 4,442,133, surfactants such as tridodecyl methyl ammonium chloride (TDMAC) and benzalconium (BZK) may be used to firmly bind a negatively-charged molecule to a hydrophobic substrate. While an anchor molecule, and in particular TDMAC, is preferred, it should be recognized that other methods of attachment are possible. For example, the medical device may be manufactured with or otherwise provided with positive surface charges. Heparin molecules then may be secured to the medical device via ionic interaction between the negatively-charged heparin and the positive surface charges on the medical device. The heparin molecules also could be immobilized onto the medical device by radiation or various cross-linking reagents, such as cyanogen bromide.

Suitable cationic antibiotics include those classified as polypeptides, aminoglycosides, and bases. Among the polypeptides are bacitracin, polymyxins, tyrothricin, viomycin, vancomycin, and their derivatives. Aminoglycosides include neomycin, erythromycin, streptomycin, tobramycin, gentamicin, kanamycin, paromomycin, and their derivates. Bases include cycloserine, tetracycline, aureomycin, terramycin, subtilin amisomycin, and their derivatives.

It is preferable to react a sodium, potassium or any monovalent alkali metal form of the negatively-charged group with a salt form of the cationic antibiotic. Thus, $OSO_3Na$, $OSO_3K$, $SO_3Na$, $SO_3K$, $OPO_3Na$ and $OPO_3K$ are preferred as negatively-charged groups, although others as for example $(OSO_3)_2Mg$, $(OSO_3)_2Ca$, $(SO_3)_2Zn$ and $(OPO_3)_2Ca$ may be used. Commercially available heparin or TDMAC heparin may contain $OSO_3$ groups in various forms, e.g., $OSO_3H$, $OSO_3Na$, $OSO_3K$, $(OSO_3)_2CA$, etc., and, as illustrated in Examples Nos. 2, and 4, steps may be taken to ensure conversion of all $OSO_3$ groups into $OSO_3Na$ or $OSO_3K$. Preferably the cationic antibiotic in salt form has at least one amine group or a net pKa of greater than 7.0. Suitable salt forms of cationic antibiotics include cationic antibiotic—$H_2OSO_3$, $HNO_3$, $HCl$, etc., as for example, tetracycline-HCl and polymixin B-sulfate.

If the negatively charged group is in acid form, as for example $OSO_3H$, $SO_3H$ and $OPO_3H$, it is preferable to react the negatively charged group with a base form of the cationic antibiotic.

The foregoing may be more particularly illustrated by the following examples:

EXAMPLE 1

One 10—mm by medical grade latex tubing obtained from Bard Urological Division of Murray Hill, New Jersey, was soaked in 50 ml of a 2% TDMAC-heparin complex solution for five seconds and air dryed for one hour. The tubing was then rinsed in 1,000 ml of distilled water for 10 minutes and then soaked in 20 ml of a 0.2% gentamicin-sulfate solution for five minutes. Subsequently, it was rinsed in 1,000 ml d.H$_2$O for 20 minutes and then air dryed at room temperature overnight.

The tubing was dipped into *E. coli* suspension in saline at $1 \times 10^6$ colony forming units per cc, (CFU/cc) for five seconds and air-dried at room temperature for 30 minutes. Then it was placed on a nutrient agar plate and incubated at 37° for 48 hours. There was no bacterial growth on and around the experimental tubing. There was heavy growth around a control.

EXAMPLE 2

One 10 mm $\times$ 10 mm polyethylene film obtained from Bard Urological Division was soaked in 50 ml TDMAC-Heparin solution for two hours and then air-dried at room temperature for one minute. The film was immersed in 1,000 ml of 0.1% sodium carbonate for five minutes and rinsed in two volumes of 1,000 ml d.H$_2$O for five minutes each with stirring. It was then immersed in 0.2% polymyxin-B sulfate solution in d.H$_2$O for three minutes with stirring, rinsed in 1,000 ml d.H$_2$O for one minute and air-dried at room temperature for one hour.

The film was dipped into *staphlococcus aureus* suspension in saline at $1 \times 10^6$ CFU/cc for five seconds and air-dried at room temperature for 30 minutes. Then it was placed on a nutrient agar plate and incubated at 37° C. for 48 hours. No growth was detected on or around the experimental film.

EXAMPLE 3

Dipped a 20 mm×30 mm medical grade PVC film in 20 ml TDMAC-Heparin solution for one minute and air-dried at room temperature for five minutes. It was then rinsed in 1,000 ml d.H$_2$O for 10 minutes, dipped into 20 ml of 0.2% tetracycline -HCl solution for three minutes and rinsed in 1,000 ml d.H$_2$O for 10 minutes.

The dry film was dipped in 2 cc of *E. coli* suspension in saline at $1 \times 10^6$ CFU/cc and then air-dried at room temperature for 30 minutes. It was then placed on a nutrient agar plate and incubated at 37° C. for 48 hours. No bacterial growth was visible both microscopically and macroscopically on or around the experimental film.

EXAMPLE 4

One 1.5 mm×10 mm×10 mm Dacron felt was soaked in 50 ml 2% TDMAC-Heparin for two hours and air-dried at room temperature for one hour. The felt was immersed in 1,000 ml 0.1% sodium bicarbonate solution for five minutes, two volumes of 1,000 ml d.H$_2$O for five minutes each, 20 ml 0.2% polymyxin-B sulfate for three minutes, and then in 1,000 nl d.H$_2$O for five minutes.

The felt was air-dried at room temperature overnight and dipped into 2 cc of *Staphlococcus aureus* at $1 \times 10^6$ CFU/cc for three seconds. It was then air-dried, placed on a nutrient agar plate and incubated at 37° C. for 48 hours. No bacterial growth was visible on or around the experimental felt.

EXAMPLE 5

A three mm piece of silicone catheter obtained from Bard Urological Division of Murray Hill, New Jersey, is soaked in 50 ml of 5% BZK-heparin in isopropanol for 5 seconds and then air dryed at room temperature for 30 minutes. It is then soaked in 10 mm of 0.1% tetracycline-HCl solution for five minutes at room temperature. Subsequently it is rinsed in 500 ml of distilled water with stirring for 30 seconds and then air dryed.

The silicon catheter is subsequently placed in a petri dish containing *E. coli* and incubated for 48 hours. The catheter inhibits the growth of *E. coli*.

It should be understood that the foregoing description of the invention is intended merely as illustrative thereof and other modifications and embodiments may be apparent to those skilled in the art without departing from its spirit.

Having thus described the invention, what I desire to claim and secure by letters patent is:

1. A medical device having long-lasting bactericidal properties comprising,
    a substrate,
    heparin molecules ionically bound to said substrate via anchor molecules, said anchor molecules attached directly to said substrate and interposed between said heparin molecules and said substrate, said anchor molecules selected from the group consisting of BZK and TDMAC, and
    cationic antibiotic molecules ionically bound to said heparin molecules.

2. A medical device as claimed in claim 1 wherein more than one cationic antibiotic molecule is bound to each molecule of heparin.

3. A medical device as claimed in claim 1 wherein said cationic antibiotic is an aminoglycoside or a polypeptide antibiotic.

4. A medical device as claimed in claim 1 wherein said cationic antibiotic is selected from the group consisting of Polymyxin B and Gentamicin.

5. In a medical device prepared from a substrate, a method of imparting said medical device with long-lasting bactericidal properties comprising,
    attaching anchor molecules selected from the group consisting of BZK and TDMAC directly to said substrate by soaking said substrate in a solution containing said anchor molecules,
    next soaking said substrate in a solution containing heparin molecules in monovalent metal salt form to ionically bind said heparin molecules to said anchor molecules on said substrate, and
    then soaking said substrate in a solution containing a salt form of cationic antibiotic molecules to bind said cationic antibiotic molecules to said heparin.

6. A method as claimed in claim 5 further characterized by binding more than one cationic antibiotic molecule to each molecule of heparin.

* * * * *